(12) United States Patent
Nishijima et al.

(10) Patent No.: US 8,775,053 B2
(45) Date of Patent: Jul. 8, 2014

(54) CONTROL DEVICE FOR INTERNAL COMBUSTION ENGINE

(75) Inventors: Hiroki Nishijima, Suntou-gun (JP); Tatsuhiro Hashida, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 13/384,975

(22) PCT Filed: Aug. 17, 2010

(86) PCT No.: PCT/JP2010/063883
§ 371 (c)(1),
(2), (4) Date: Jan. 19, 2012

(87) PCT Pub. No.: WO2012/023182
PCT Pub. Date: Feb. 23, 2012

(65) Prior Publication Data
US 2013/0144503 A1    Jun. 6, 2013

(51) Int. Cl.
*F01N 3/021* (2006.01)
*F02D 41/14* (2006.01)
*F01N 3/00* (2006.01)

(52) U.S. Cl.
CPC ........ *F02D 41/1494* (2013.01); *F01D 2560/05* (2013.01); *F01N 2560/20* (2013.01)
USPC ............................................ 701/102; 60/276

(58) Field of Classification Search
CPC ............ F01N 2560/20; F01N 2560/05; F02D 41/1494
USPC ............ 701/102, 109, 114; 60/276, 286, 320; 73/28.01, 23.33; 96/19; 324/705
See application file for complete search history.

(56) References Cited

U.S. PATENT DOCUMENTS

| | | |
|---|---|---|
| 2007/0264158 A1 | 11/2007 | Schmidt et al. |
| 2008/0024111 A1 | 1/2008 | Dorfmueller et al. |
| 2010/0000404 A1 | 1/2010 | Sakuma et al. |
| 2010/0000863 A1* | 1/2010 | Kondo et al. ............ 204/406 |
| 2012/0233987 A1* | 9/2012 | Aoki et al. ............ 60/320 |

FOREIGN PATENT DOCUMENTS

| | | |
|---|---|---|
| DE | 4139325 C1 | 1/1993 |
| EP | 1624166 A1 | 2/2006 |
| JP | Y2-03-48527 | 10/1991 |

(Continued)

OTHER PUBLICATIONS

Nov. 9, 2010 International Search Report issued in Patent Application No. PCT/JP2010/063883 (with translation).

*Primary Examiner* — Mahmoud Gimie
(74) *Attorney, Agent, or Firm* — Oliff PLC (57) ABSTRACT

An internal combustion engine control device having a particulate matter sensor which has a pair of electrodes disposed at a distance from each other and measures the amount of particulate matter in a gaseous body, and elimination means for burning and eliminating particulate matter attached to the particulate matter sensor. The control device performs a particulate matter elimination process to judge whether the amount of particulate matter attached to the particulate matter sensor is smaller than a reference particulate matter amount that is predefined as the minimum amount of remaining particulate matter required to bring the pair of electrodes into electrical conduction at one or more spots. When the amount of particulate matter is judged to be smaller than the reference particulate matter amount, the control device causes the elimination means to terminate the particulate matter elimination process.

21 Claims, 6 Drawing Sheets

(56) References Cited

FOREIGN PATENT DOCUMENTS

| | | |
|---|---|---|
| JP | A-2008-523367 | 7/2008 |
| JP | A-2008-190502 | 8/2008 |
| JP | A-2009-144512 | 7/2009 |
| JP | A-2009-144577 | 7/2009 |
| JP | A-2010-151554 | 7/2010 |
| JP | A-2010-156698 | 7/2010 |
| WO | WO 2005/124326 A1 | 12/2005 |
| WO | WO 2006/061278 A1 | 6/2006 |
| WO | WO 2008/111677 A1 | 9/2008 |

* cited by examiner

CONTROL DEVICE FOR INTERNAL COMBUSTION ENGINE

TECHNICAL FIELD

The present invention relates to a control device for an internal combustion engine. More specifically, the present invention relates to an internal combustion engine control device having a particulate matter sensor that is installed in an exhaust path of an internal combustion engine to detect the amount of particulate matter in exhaust gas.

BACKGROUND ART

As disclosed in Patent Document 1, a sensor is conventionally known that detects the amount of particulate matter (hereinafter may be referred to as PM) in exhaust gas of an internal combustion engine. The sensor disclosed in Patent Document 1 includes an insulation layer on which the PM is to be deposited, and a pair of electrodes which are disposed on the insulation layer with those positioned apart from each other. When the sensor comes into contact with the exhaust gas so that the PM in the exhaust gas is accumulated between the electrodes, electrical conductivity between the electrodes changes in accordance with the amount of accumulated PM, thereby changing the resistance between the electrodes. Therefore, when changes in the resistance between the electrodes are detected, the amount of PM accumulated between the electrodes is detected. Thus, the amount of PM in the exhaust gas is estimated.

When the amount of accumulated PM exceeds a certain value, the resistance value between the electrodes does not change anymore so that the sensor is no longer able to generate an output value in accordance with the amount of 1, accumulated PM. A technology disclosed in Patent Document on the other hand, performs a PM reset by heating the sensor for a predetermined period of time with a heater built in the sensor to burn and eliminate the accumulated PM when the amount of accumulated PM is increased.

PRIOR ART LITERATURE

Patent Documents

Patent Document 1: JP-A-2009-144577
Patent Document 2: JP-A-2009-144512

SUMMARY OF THE INVENTION

Problem To Be Solved By the Invention

The technology disclosed in Patent Document 1 heats the sensor for a predetermined period of time to burn and eliminate the PM. When this PM reset is performed, the PM accumulated on the insulation layer is eliminated completely or almost completely. However, the heater generally consumes a large amount of electrical power to eliminate the PM accumulated on the sensor virtually completely. It is therefore desired that the amount of such power consumption be reduced.

Further, when the PM is eliminated virtually completely by the PM reset, there is no electrical conduction between the sensor electrodes. For a certain period of time after the PM reset, therefore, the electrodes are insulated from each other to exhibit a high resistance. Thus, the resulting sensor output value is close to 0 (zero). In other words, the sensor output cannot be obtained in accordance with the amount of accumulated PM until the PM is accumulated between the electrodes to form an electrically conductive path between the electrodes through the PM, after the PM reset. Hence, changes in the amount of PM in the exhaust gas cannot be determined before the electrodes are brought into electrical conduction.

Therefore, when, for instance, a PM filter installed upstream of the sensor becomes defective, the amount of PM in the exhaust gas may drastically increase within a short period of time. However, when the above-described conventional PM reset is performed, such an extraordinary change in the amount of PM may not be detected for a certain period of time after the PM reset. The failure to detect such a change in the amount of PM should be avoided. It is demanded that the amount of PM be consistently determined for a longer period of time.

An object of the present invention is to solve the above problem and provide an improved internal combustion engine control device that is capable of detecting the amount of PM in accordance with a sensor output even immediately after the elimination of PM while reducing the amount of electrical power consumed to eliminate the PM accumulated on a sensor element section.

Means For Solving the Problem

In accomplish the above object, according to a first aspect of the present invention, there is provided a control device for an internal combustion engine, including: a particulate matter sensor that includes a pair of electrodes disposed at a distance from each other and measures an amount of particulate matter in a gaseous body; elimination means for burning and eliminating particulate matter attached to the particulate matter sensor; particulate matter amount judgment means for judging whether the amount of particulate matter attached to the particulate matter sensor is smaller than a reference particulate matter amount that is predefined as a minimum amount of remaining particulate matter required to bring the pair of electrodes into electrical conduction at one or more spots; and elimination process control means for causing the elimination means to terminate a process of eliminating the particulate matter when the amount of particulate matter is judged to be smaller than the reference particulate matter amount.

According to a second aspect of the present invention, there is provided control device as described in the first aspect, the control device further including reference time setup means for setting, as a reference time, a time required for the elimination process to decrease the amount of particulate matter to the reference particulate matter amount in accordance with an operating status of the internal combustion engine. The particulate matter amount judgment means judges whether the amount of particulate matter is smaller than the reference particulate matter amount by determining whether the elimination process is performed for the reference time.

According to a third aspect of the present invention, there is provided control device as described in the first or the second aspect, the control device further including sensor output detection means for detecting an output of the particulate matter sensor. The particulate matter amount judgment means judges whether the amount of particulate matter is smaller than the reference particulate matter amount by determining whether the output of the particulate matter sensor is lower than a reference output that is set as a particulate matter sensor output that is equivalent to the reference particulate matter amount.

According to a fourth aspect of the present invention, there is provided control device as described in the third aspect, the control device further including: temperature detection means for detecting a temperature of an element section of the particulate matter sensor; and reference output setup means for setting the reference output in accordance with the temperature detected by the temperature detection means.

According to a fifth aspect of the present invention, there is provided control device as described in the first or the second aspect, the control device further including: temperature detection means for detecting a temperature of the particulate matter sensor; and
heat generation amount calculation means for calculating an amount of heat generated by the particulate matter sensor in accordance with the temperature detected by the temperature detection means. The particulate matter amount judgment means judges whether the amount of particulate matter is smaller than the reference particulate matter amount by determining whether the amount of generated heat is larger than a reference heat generation amount.

According to a sixth aspect of the present invention, there is provided control device as described in the first or the second aspect, the control device further including: temperature detection means for detecting a temperature of the particulate matter sensor; heat generation amount calculation means for calculating an amount of heat generated by the particulate matter sensor in accordance with the temperature detected by the temperature detection means; and integrated heat generation amount detection means for detecting an integrated amount of heat generated since a beginning of the elimination process. The particulate matter amount judgment means judges whether the amount of particulate matter is smaller than the reference particulate matter amount by determining whether the integrated amount is larger than a reference integrated heat generation amount.

According to a seventh aspect of the present invention, there is provided control device as described in the first or the second aspect, the control device further including: temperature detection means for detecting a temperature of the particulate matter sensor; and temperature change calculation means for calculating change in the temperature of the particulate matter sensor. The particulate matter amount judgment means judges whether the amount of particulate matter is smaller than the reference particulate matter amount by determining whether the temperature change is smaller than a reference temperature change amount.

According to a eighth aspect of the present invention, there is provided control device as described in the any one of the fourth to the seventh aspect, wherein the temperature detection means is a temperature sensor that is installed near the pair of electrodes of the particulate matter sensor.

According to a ninth aspect of the present invention, there is provided control device as described in the any one of the first to the eighth aspect, wherein the elimination means is a heater installed near the pair of electrodes; and wherein the elimination process control means supplies electrical power having a fixed pulse width to the heater to heat the pair of electrodes and burn the particulate matter.

According to a tenth aspect of the present invention, there is provided control device as described in the any one of the first to the ninth aspect, wherein the elimination means is a heater installed near the pair of electrodes; wherein the pair of electrodes each have a dense area where the electrodes are relatively densely disposed; and wherein the heater mainly heats the dense area of the pair of electrodes.

Advantages of the Invention

According to the first aspect of the present invention, the process of eliminating the particulate matter is terminated when the amount of particulate matter is smaller than a reference particulate matter amount that is predefined as the minimum amount of remaining particulate matter required to bring the pair of electrodes into electrical conduction at one or more spots. Hence, even immediately after the process of eliminating the particulate matter, the sensor output changes in accordance with the amount of accumulated particulate matter. Therefore, the measurement of the amount of particulate matter in a gaseous body can be resumed immediately after the process of eliminating the particulate matter. Further, as the elimination process terminates at a timing when the amount of remaining particulate matter is equal to the reference particulate matter amount, the duration of the elimination process can be minimized. This makes it possible to let the particulate matter sensor measure the amount of particulate matter for an increased period of time and reduce, for instance, the amount of electrical power consumed to perform the elimination process.

According to the second aspect of the present invention, the duration of the elimination process for decreasing the amount of particulate matter to the reference particulate matter amount is set in accordance with the operating state, and the timing when the elimination process terminates is determined on the basis of the duration of the elimination process. Therefore, the elimination process can be performed for an optimum period of time in accordance with the operating state. In addition, the elimination process can be terminated with increased certainty when the amount of remaining particulate matter is equal to the reference particulate matter amount. Further, as the duration of the elimination process can be set as described above to ensure that it is optimized and is no more than adequate, the amount of electrical power consumed to perform the elimination process is minimized.

According to the third aspect of the present invention, whether the elimination process should be terminated is determined by judging whether the output of the particulate matter sensor is lower than the predefined reference output. The reference output is set as a sensor output that is equivalent to the reference particulate matter amount. Therefore, the elimination process can be terminated unfailingly at an optimum timing when the amount of remaining particulate matter is equal to the reference particulate matter amount.

According to the fourth aspect of the present invention, the reference output, which is used as the basis for determining whether the elimination process should be terminated, can be set in accordance with the temperature of the element section of the particulate matter sensor. Therefore, even when the temperature of the particulate matter sensor varies greatly during the elimination process, the reference output, which serves as the basis for determination, can be set to an output value that corresponds to the reference particulate matter amount prevailing at the temperature. Consequently, the elimination process can be terminated at a better timing.

According to any one of the fifth to seventh aspects of the present invention, the amount of heat generated by the particulate matter sensor, the cumulative amount of heat generated by the particulate matter sensor, or a change in the temperature of the particulate matter sensor is detected in accordance with a detected temperature of the particulate matter sensor. Further, the timing at which the process of eliminating the particulate matter is terminated is determined. When the process of eliminating the particulate matter is performed, heat generation occurs in accordance with the amount of burned particulate matter. Therefore, the timing at which the elimination process terminates can be properly determined in accordance with the amount of heat generated by the particulate matter sensor, the cumulative amount of heat generated by the particulate matter sensor, or a change in the temperature of the particulate matter sensor.

According to the eighth aspect of the present invention, the temperature sensor installed near the pair of electrodes detects a temperature. Therefore, changes in the temperature of the electrodes and the amount of heat generated by the electrodes can be detected with increased accuracy.

According to the ninth aspect of the present invention, the elimination process is performed by supplying electrical power having a fixed pulse width to the heater. As this makes it possible to locally heat the electrodes for a short period of time, the amount of electrical power consumption can be reduced.

According to the tenth aspect of the present invention, the heater mainly heats an area where the pair of electrodes are relatively densely disposed. Therefore, the electrodes can be heated with increased efficiency during the elimination process. This makes it possible to reduce the amount of electrical power consumed during the elimination process.

MODE FOR CARRYING OUT THE INVENTION

Embodiments of the present invention will now be described with reference to the accompanying drawings. In each of the drawings, identical or corresponding parts or elements will be designated by the same reference numerals to simplify or omit the description thereof.

First Embodiment

Overall System Configuration of First Embodiment

Figure 1:
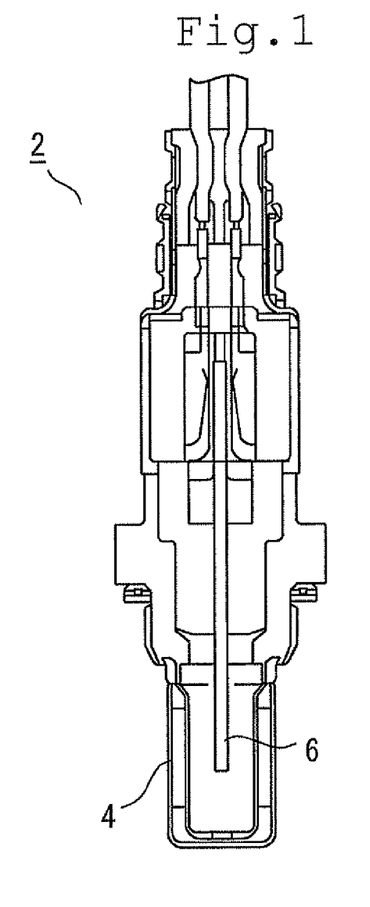
FIG. 1 is schematic diagram illustrating a PM sensor according to the first embodiment of the present invention.
Figure 2:
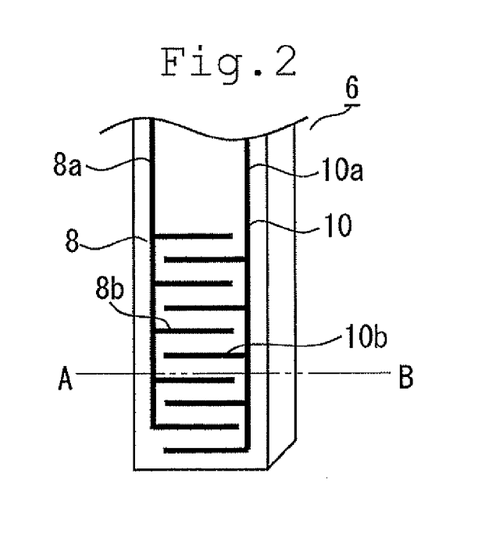
FIG. 2 is schematic diagram illustrating a configuration of a sensor element section of the PM sensor according to the first embodiment of the present invention.

FIGS. 1 and 2 are schematic diagrams illustrating a PM sensor (particulate matter sensor) according to an embodiment of the present invention. FIG. 1 is an overall view of the PM sensor. FIG. 2 is a partially enlarged view of a sensor element section. As shown in FIG. 1, the PM sensor 2 includes a cover 4 and an element section 6 which is positioned in a space inside the cover 4. The cover 4 has a plurality of holes that permits a gaseous body to pass therethrough. When the PM sensor 2 is used, the cover 4 is placed in an exhaust path of an internal combustion engine so that an exhaust gas flows into the cover 4 through the plurality of holes in the cover 4. The element section 6 is then brought into contact with the exhaust gas.

As shown in FIG. 2, a pair of electrodes 8, 10 are mounted on a surface of the element section 6. The pair of electrodes 8, 10 are not in contact with each other and are disposed at a predetermined distance from each other. The electrodes 8, 10 each have a dense area where the electrodes are relatively densely disposed. More specifically, the electrodes 8, 10 each include an electrically-conductive part 8a, 10a, which is disposed in an area other than the dense area and extended in the longitudinal direction of the element section 6. Meanwhile, the dense area, which is positioned close to the leading end of the element section 6, includes the electrically-conductive parts 8a, 10a and a plurality of electrically-conductive parts 8b, 10b, which are formed in a direction perpendicular to the electrically-conductive parts 8a, 10a. In other words, the electrodes 8, 10 each have the electrically-conductive parts 8b, 10b that are arranged in the dense area of the element section 6 to form a comb-shaped structure. The comb-shaped portions are disposed to mesh with each other.

Figure 3:
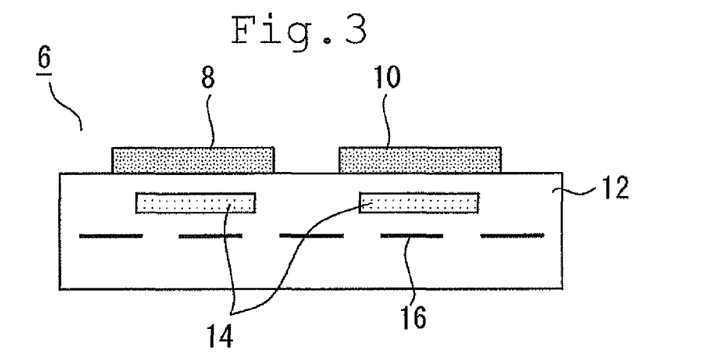
FIG. 3 is schematic diagram illustrating a configuration of a sensor element section of the PM sensor according to the first embodiment of the present invention.

FIG. 3 is a schematic diagram illustrating a cross section taken along line A-B of FIG. 2. The upper portion of FIG. 3 corresponds to the surface side of the element section 6 shown in FIG. 2. As shown in FIG. 3, the electrodes 8, 10 are disposed in contact with an insulation layer 12. The insulation layer 12 functions so that PM (particulate matter) adheres to it. Thermocouples or other temperature sensors 14 (temperature detection means), which relate to the electrodes 8 and 10, are embedded in the insulation layer 12 and positioned at close proximity to the electrodes 8 and 10.

A heater 16 (elimination means) is embedded beneath the temperature sensors 14. The heater 16 is formed so that the center of its heat generation is positioned directly below the dense area of the electrodes 8, 10 in order to efficiently heat the dense area in particular.

The electrodes 8, 10 are connected to a power source (not shown) through their respective power supply circuits or the like. Thus, a voltage can be applied between the electrodes 8 and 10. When a detector (not shown) detects an output (electrical current value) generated upon voltage application, the amount of PM in the exhaust gas can be determined in accordance with the corresponding resistance value between the electrodes 8 and 10.

The temperature sensors 14 are connected to detectors (not shown) which detect electromotive force generated in the temperature sensors 14, through a predetermined circuit. Temperatures prevailing near the electrodes 8, 10 can be detected by detecting the electromotive force of the temperature sensors 14. Further, the heater 16 is connected to a power source (not shown) through a power supply circuit or the like. When predetermined electrical power is supplied to the heater 16, the heater heats the element section 6 including the electrodes 8, 10.

The above detectors and the power supply circuits or the like are connected to a control device (not shown). The control device detects, for instance, the amount of PM in accordance with a detector output, calculates values in accordance with various sensor outputs, and supplies control signals to the power supply circuits or the like to control, for instance, the supply of electrical power to the electrodes 8, 10 and the heater 16.

In the first embodiment, the control device provides control over, for instance, the detection of the amount of PM and the process of eliminating accumulated PM (hereinafter referred to as the "PM reset").

[Detecting the Amount of PM]

Figure 4:
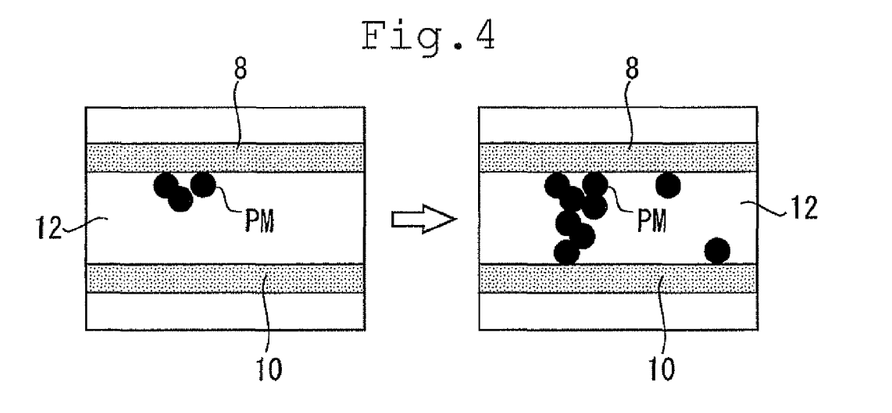
FIG. 4 is a set of diagrams illustrating how the PM is accumulated on the PM sensor according to the first embodiment of the present invention.

FIG. 4 is a set of diagrams illustrating how the PM is accumulated on the element section 6. Immediately after the conventional PM reset, where the PM between the electrodes 8 and 10 is virtually completely eliminated (or in an initial sensor state), almost no PM is accumulated between the electrodes 8 and 10 as indicated in the left-hand diagram of FIG. 4. In this state, there is no electrical conduction between the electrodes 8 and 10. Therefore, even when a predetermined voltage for sensor output detection is applied between the electrodes 8 and 10, the output (electrical current value) of the PM sensor 2 is close to 0 (zero). While the electrodes 8, 10 are insulated from each other as described above, the PM sensor 2 does not exhibit a significant change no matter whether the amount of accumulated PM changes to a certain extent.

However, when the PM sensor 2 comes into contact with the exhaust gas, the PM is gradually accumulated between the electrodes 8 and 10. As indicated in the right-hand diagram of FIG. 4, the accumulated PM brings one or more spots of the electrodes 8, 10 into electrical conduction. In this state, the sensor output begins to change in accordance with changes in the electrical conduction between the electrodes 8 and 10. In other words, the sensor output begins to change in accordance with the amount of PM accumulated between the electrodes 8 and 10. In the resulting state, the control device applies a predetermined voltage between the electrodes 8 and 10, detects the resulting electrical current as the sensor output, determines the corresponding resistance value between the electrodes 8 and 10, and estimates the amount of PM in the exhaust gas of the internal combustion engine in accordance with the determined resistance value.

[PM Reset In First Embodiment]

When the amount of PM accumulated between the electrodes 8 and 10 of the PM sensor 2 is further increased until it is saturated, the PM sensor 2 no longer exhibits further output changes. In this state, the amount of PM cannot be properly measured. Therefore, the control device performs the PM reset in order to eliminate the PM accumulated between the electrodes 8 and 10 before saturation. More specifically, the control device flows a predetermined DC current to the heater 16 to raise the temperature of the element section 6 to approximately 800° C. The accumulated PM is then burned and eliminated.

However, if electrical power is supplied in a conventional manner until the PM is completely eliminated, PM does not exist to form an electrically conductive path between the electrodes 8 and 10 (see the left-hand diagram of FIG. 4). As a result, the sensor output between the electrodes 8 and 10 substantially remains close to 0 (zero). Therefore, even if the amount of accumulated PM changes, the sensor output does not exhibit a significant change until the PM is accumulated to form an electrically conductive path between the electrodes 8 and 10. It means that an increase in the amount of PM cannot be detected during a period during which an electrically conductive path is not formed between the electrodes 8 and 10. For descriptive purposes, this period may be hereinafter referred to as the "dead zone."

The system according to the first embodiment controls the time of the PM reset so that the dead zone does not arise. More specifically, the system terminates the PM reset when a "reference time" elapses. The reference time elapses when the amount of PM is decreased to a reference PM amount (reference particulate matter amount) that meets conditions (A) and (B) below:

(A) The amount of PM that allows the PM to form an electrically conductive path between the electrodes 8 and 10 at one or more spots (B) The minimum amount of PM that allows the sensor output to exhibit significant changes in accordance with changes in the amount of accumulated PM even immediately after the PM reset The method of setting the reference time for the PM reset will be described below.

[Reference Time Setup In First Embodiment]

Figure 5:
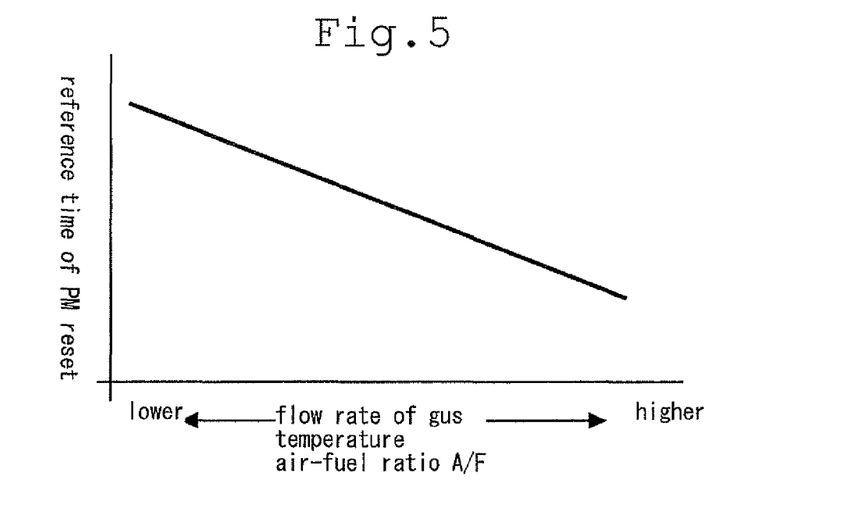
FIG. 5 is a graph illustrating the relationship between the reference time and the operating status of the internal combustion engine according to the first embodiment of the present invention.

FIG. 5 is a graph illustrating the relationship between the reference time and the operating status of the internal combustion engine according to the first embodiment of the present invention. Referring to FIG. 5, when a gaseous body flow rate or an air-fuel ratio A/F is high, there is an increase in the amount of oxygen circulating in the exhaust path in which the PM sensor 2 is installed. This facilitates the combustion of PM during the PM reset. Therefore, the higher the gaseous body flow rate or the air-fuel ratio A/F, the shorter the reference time setting. Further, a high gaseous body temperature also facilitates the combustion of PM. Hence, the higher the gaseous body temperature, the shorter the reference time setting.

Moreover, the larger the amount of accumulated PM, the longer the time required for burning and eliminating the PM. Thus, the larger the amount of accumulated PM, the longer the reference time setting. The amount of accumulated PM can be estimated by detecting the sensor output prevailing immediately before the start of the PM reset.

The optimum reference time adapted, for instance, to the gaseous body flow rate, the air-fuel ratio, an exhaust gas temperature, or the amount of accumulated PM (sensor output) can be predetermined by experiment or the like. In other words, the optimum time required for decreasing the amount of accumulated PM to the reference PM amount can be determined as the reference time for each combination of the operating status and the amount of accumulated PM. The relationship between the operating status, the amount of accumulated PM, and the reference time, which is determined as described above, is stored as a map in the control device. During actual control, the control device detects, for instance, the current gaseous body flow rate, the current air-fuel ratio, the current exhaust gas temperature, and the current amount of accumulated PM, and uses the map to set the reference time in accordance with the detected values.

Figure 6:
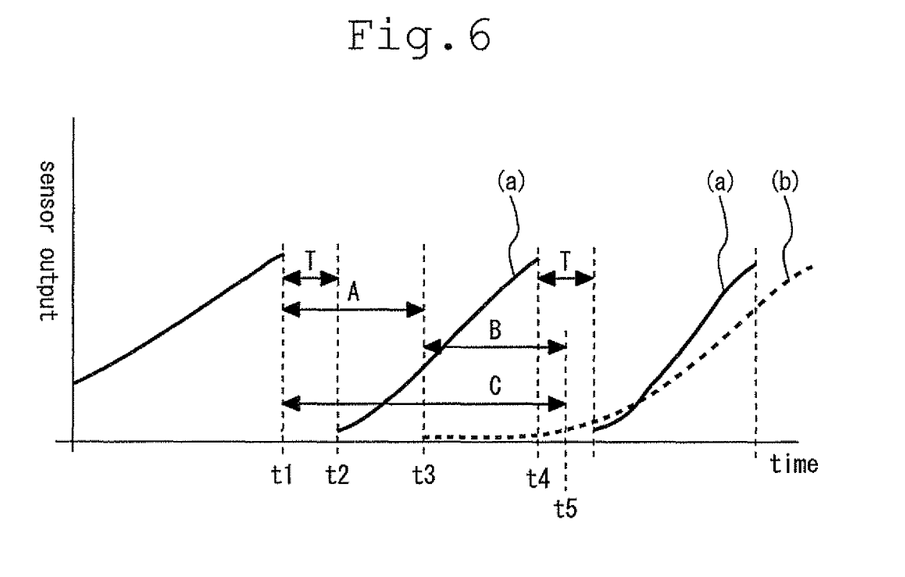
FIG. 6 is a graph illustrating how the sensor output changes when the PM reset is performed in the first embodiment of the present invention.

FIG. 6 is a graph illustrating how the sensor output changes when the PM reset is performed in the first embodiment. In FIG. 6, the horizontal axis represents time whereas the vertical axis represents the sensor output. Solid lines (a) in FIG. 6 indicate the sensor output prevailing when the PM reset is performed in accordance with the first embodiment. For comparison purposes, the broken line (b) in FIG. 6 indicates the sensor output prevailing when the conventional PM reset is performed.

At first, the PM reset starts at time t1, as shown in FIG. 6, when the amount of accumulated PM is judged to be saturated. In the first embodiment, the reference time T is the time for equalizing the remaining amount of PM with the reference PM amount. Therefore, the reference time T is shorter than time A, which is the time of the conventional PM reset.

At time t2, which arrives when the reference time T elapses after time t1, the initial PM reset according to the first embodiment terminates. At this time, the amount of PM remaining between the electrodes 8 and 10 is equal to the reference PM amount so that an electrically conductive path is formed at one or more spots. Therefore, after an elapse of the reference time T, the sensor output immediately exhibits a change in accordance with the amount of accumulated PM. Subsequently, until time t4 at which the PM sensor 2 is saturated again, the amount of PM can be detected in accordance with the output of the PM sensor 2.

When, on the other hand, a conventional elimination process is performed for a period of reference time A, which is relatively long, to completely eliminate the PM, dead zone B, during which the output of the PM sensor 2 remains unchanged, persists until time t5 at which the PM is accumulated again to form an electrically conductive path between the electrodes 8 and 10 after an elapse of reference time A. In other words, when the conventional PM reset is performed, the PM sensor cannot detect the amount of accumulated PM for total period C which is determined by adding reference time A to dead zone B. On the other hand, performing the PM reset according to the first embodiment makes it possible to eliminate the dead zone of the PM sensor 2, effectively use the PM sensor 2, and detect the amount of PM during a period other than a short PM reset time.

Meanwhile, reference time T is set in accordance with the operating status as described above. However, if the operating status suddenly changes during the PM reset, the amount of accumulated PM may not decrease to the reference PM amount even when the PM reset is performed for initially set reference time T. In such a case, too, the PM sensor output changes in accordance with the amount of PM as far as the PM is eliminated to a certain extent. However, it is preferred that the amount of accumulated PM be decreased to the predetermined reference PM amount when the PM reset is performed.

Therefore, when the amount of accumulated PM is not decreased to the reference PM amount after the PM is reset is performed for a period of reference time T, the PM reset is continuously performed until the amount of accumulated PM decreases to the reference PM amount. More specifically, when the output of the PM sensor 2 is not lower than the reference output after the PM reset is performed for a period of reference time T, the remaining amount of accumulated PM is detected again in accordance with the current PM sensor output. Further, the operating status is detected to set reference time T again in accordance with the detected items of information. Subsequently, the PM reset is continuously performed until re-set reference time T elapses. In this instance, the reference output is set to be equivalent to a sensor output that is generated at a temperature prevailing during the PM reset while the amount of accumulated PM is equal to the reference PM amount.

[Details of Control Exercised In First Embodiment]

Figure 7:
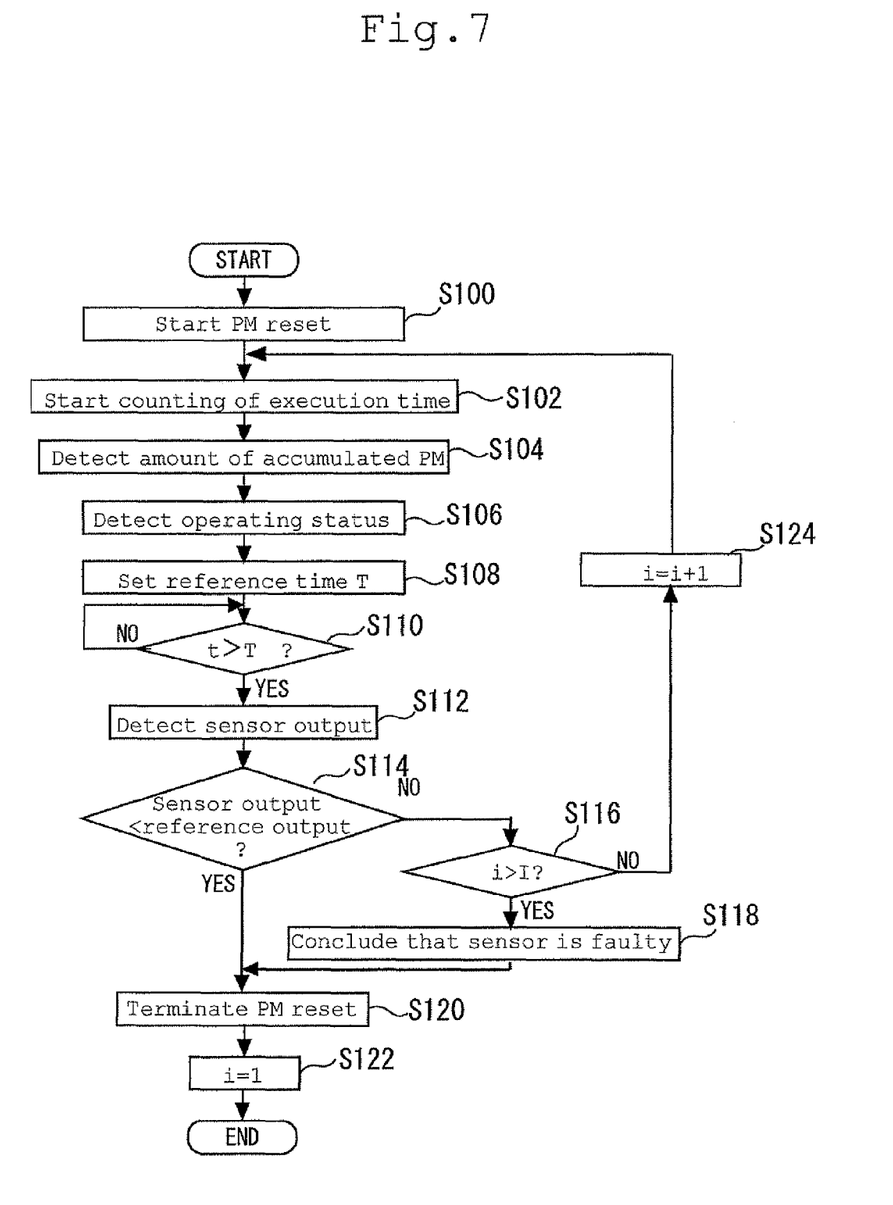
FIG. 7 is a flowchart illustrating a control routine that is executed by the control device according to the first embodiment of the present invention.

FIG. 7 is a flowchart illustrating a control routine that is executed by the control device according to the present invention. The routine shown in FIG. 7 is executed when a command for performing a PM elimination process is issued.

When a command for performing the PM reset is issued, the routine shown in FIG. 7 first performs the PM reset (step S100). The PM reset begins when the control device issues a signal to apply a predetermined voltage to the heater 16, thereby causing a DC current to flow to the heater 16. The electrodes 8, 10 are then heated so that the PM accumulated between the electrodes 8 and 10 is gradually eliminated. While the PM reset is performed, the element temperature is raised to approximately 800° C.

Next, the routine starts the counting of PM reset execution time t (step S102). The execution time t is counted to indicate the elapsed time after the start of the counting. Next, the routine detects the amount of currently accumulated PM (step S104). In step S104, the control device calculates the amount of accumulated PM in accordance with the current output of the PM sensor 2 and the current output values of the temperature sensors 14.

Next, the routine detects the current operating status of the internal combustion engine (step S106). As the operating status, operating states serving as parameters necessary for determining the reference time are detected. In the first embodiment, the air-fuel ratio A/F based on the output of an A/F sensor (not shown), the gaseous body flow rate based on the output of an air flow meter (not shown), and the exhaust gas temperature based on the outputs of the temperature sensors installed in the exhaust path are detected.

Next, the routine sets the reference time T for the PM reset (step S108). The map stored in the control device is used to calculate the reference time T in accordance with the amount of accumulated PM which is detected in step S104, and with the detected values representing the operating states detected in step S106.

Next, the routine performs step S110 to judge whether the PM reset execution time t is longer than the reference time T. In step S110, the routine judges whether the PM reset is performed for a period longer than the reference time T which is defined to ensure that the amount of PM remaining between the electrodes 8 and 10 is equal to the reference PM amount, that is, the minimum required PM amount. When the judgment result obtained in step S110 does not indicate that the execution time t is longer than the reference time T, the routine repeatedly performs step S110 until the execution time t is longer than the reference time T.

When, on the other hand, the judgment result obtained in step S110 indicates that the execution time t is longer than the reference time T, the routine proceeds to step S112 and detects the current sensor output. Next, the routine proceeds to step S114 and judges whether the sensor output is lower than the reference output. The reference output is a fixed value that is stored in the control device to represent a sensor output corresponding to the reference PM amount at a temperature (approximately 800° C.) prevailing during the PM reset or at a predefined temperature (approximately 200° C. to 800° C.)

When the judgment result obtained in step S114 does not indicate that the sensor output is lower than the reference output, the routine proceeds to step S116 and judges whether the value of a counter i is greater than a reference count I. The counter i counts the number of times the PM reset is performed in steps S102 to S116. The initial value of the counter i is set to 1. The reference count I is a reference value that is stored in the control device to judge whether the PM sensor 2 is faulty.

When the judgment result obtained in step S116 indicates that the value of the counter i is greater than the reference count I, it means that the sensor output is not decreased to the reference output corresponding to the reference PM amount after the PM reset performed for a period equal to the reference time T is repeated a number of times equal to the reference count 1. In this instance, the routine concludes that the PM sensor 2 is faulty (step S118) and performs a predetermined process, for instance, to illuminate a warning lamp.

Subsequently, the routine proceeds to step S120 and terminates the PM reset. More specifically, the routine shuts off the power supply to the heater 16. Next, the routine proceeds to step S122 and sets the counter i to its initial value 1. This brings the current process to an end.

When, on the other hand, the judgment result obtained in step S116 does not indicates that the value of the counter i is greater than the reference count I, the routine proceeds to step S124 and increments the counter i by one so that i=i+1. The routine then returns to step S102, resets the PM reset execution time t, and starts anew to count the PM reset execution time t. Subsequently, the routine performs steps S104 to S114 in the same manner as described above.

When the sensor output is found in step S114 to be lower than the reference output after completion of the above processing steps, it implies that the PM is burned and eliminated until the amount of accumulated PM is decreased to the reference PM amount. Therefore, the routine proceeds to step S120 and terminates the PM reset. More specifically, the routine shuts off the power supply to the heater 16. Next, the routine proceeds to step S122 and sets the counter i to 1. This brings the current process to an end.

As described above, the first embodiment sets the reference time T for the PM reset as appropriate in accordance with the amount of accumulated PM and the operating status. The reference time T is equivalent to a period of time during which the amount of remaining PM forms an electrically conductive path between the electrodes 8 and 10 at one or more spots. It is the time that is equivalent to a value close to the upper-limit value of a time range within which the sensor output changes in accordance with changes in the amount of accumulated PM from a point immediately after the PM reset. Therefore, changes in the amount of PM can be monitored beginning with a point immediately after the PM reset. When the minimum required short period of time is set as the reference time as described above, it is possible to reduce the amount of electrical power consumed during the PM reset.

The first embodiment has been described on the assumption that the PM reset terminates only when the sensor output is decreased to the predefined reference output after an elapse of the preset reference time T. The PM reset terminates as described above in order to provide against a case where the amount of PM cannot be reduced to the reference PM amount when the amount of burned PM is smaller than predicted amount due to a great operating status change even after an elapse of the reference time T. In other words, performing the PM reset only when the PM sensor output is decreased to the reference output makes it possible to prevent the termination of the PM reset while the amount of remaining PM is excessively large. Further, even in the above instance, the reference time is set on a case-by-case basis. This prevents the PM reset from being performed for an unduly long period of time to let the PM elimination process progress excessively.

However, the present invention is not limited to a case where, as is the case with the first embodiment, the elapse of the reference time and the sensor output are considered in conjunction with each other to determine whether the PM reset should be terminated. The PM reset may alternatively be terminated immediately when the preset reference time is found to have elapsed.

The first embodiment has been described on the assumption that the sensor output and the operating status are detected again to set the reference time T again only when the sensor output cannot be lower than the reference output. However, the present invention is not limited to the above-described setup of the reference time. For example, the current operating status may be repeatedly detected to correct the reference time T accordingly while the PM reset is performed until the reference time T is found to have elapsed. Thus, the time during which the subsequent PM reset should be performed can be corrected in accordance with the current operating status. This makes it possible to cope with operating status changes during the PM reset and perform the PM reset for a more appropriate period of time.

The first embodiment has been described on the assumption that the reference time T is set in accordance with the amount of accumulated PM, the air-fuel ratio A/F, the gaseous body flow rate, and the gaseous body temperature. However, the present invention is not limited to the use of such a method of reference time setup. Alternatively, however, the reference time may be set in accordance with one or more parameters affecting the amount of accumulated PM or the amount of burned PM.

The first embodiment has been described on the assumption that the PM sensor 2 is judged to be faulty when the sensor output is found in step S114 to be lower than the reference output a number of times equal to the reference count I. However, the present invention need not always perform such a failure diagnosis. Alternatively, the present invention may immediately conclude that the PM sensor 2 is faulty when the sensor output is once found in step S114 to be lower than the reference output.

The first embodiment has been described on the assumption that the temperature sensors 14 are embedded beneath the electrodes 8, 10. However, the present invention is not limited to the use of the PM sensor 2 having such a configuration. Alternatively, temperature detection means other than the temperature sensors 14 may be used to detect the temperature of the element section. Another alternative is to detect the temperature of the element section of the PM sensor by detecting the impedance of the PM sensor without resorting to the temperature detection means. This is also true for later-described embodiments.

Heating means for the present invention is not limited to the use of the configuration of the heater 16 described in the first embodiment. The heating means may be mounted at a different position. Further, heating means other the heater 16 may be used to heat the vicinity of the electrodes 8, 10. This is also true for the later-described embodiments.

The first embodiment has been described on the assumption that individual steps are performed for judgment purposes while a predetermined voltage is applied during PM processing to use the value of an electrical current flowing between the electrodes 8 and 10 as a sensor output. However, the present invention is not limited to the application of such a fixed voltage. Alternatively, the present invention may be applied to a case where the applied voltage varies. In such an instance, the resistance value between the electrodes 8 and 10 may be calculated in accordance with the PM sensor output to perform the individual judgment steps on the basis of the calculated resistance value. More specifically, when, for instance, a resistance value is greater than a reference resistance value in step S114 in a situation where the individual judgment steps are performed by using a resistance value corresponding to the sensor output, the PM reset is terminated as the amount of accumulated PM is found to be smaller than the reference PM amount. This is also true for the later-described embodiments.

In the first embodiment, the "reference time setup means" according to the present invention is implemented when the process in step S108 is performed; the "sensor output detection means" is implemented when the process in step S112 is performed; the "particulate matter amount judgment means" is implemented when the process in step S110 or step S114 is performed; and the "elimination process control means" is implemented when the process in step S120 is performed.

Second Embodiment

In the first embodiment, the output of the PM sensor 2 and the reference time T which is set in accordance with the operating status, are used as parameters that determine whether the PM reset should be terminated. In a second embodiment of the present invention, on the other hand, the amount of heat generated by the PM sensor 2 is used to determine whether the PM reset should be terminated.

Figure 8:
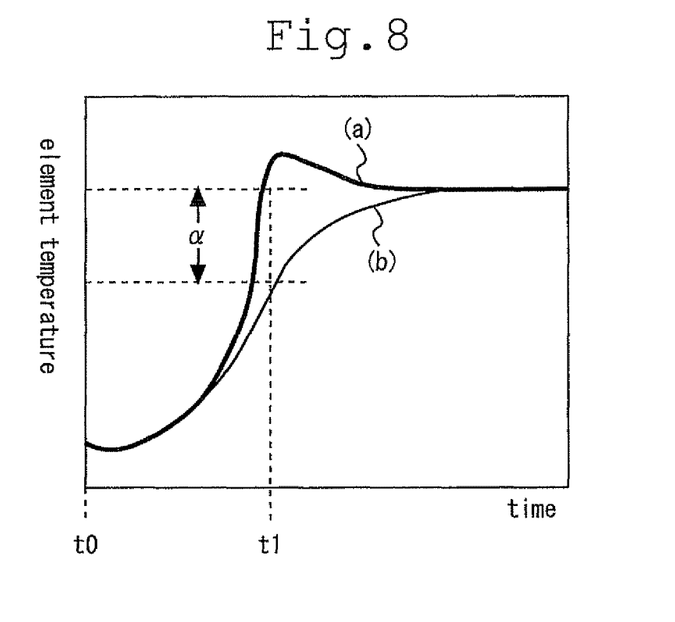
FIG. 8 is a graph illustrating the element temperature of the PM sensor during the PM reset according to second embodiment of the present invention.

FIG. 8 is a graph that relates to the second embodiment of the present invention and illustrates the relationship between the PM reset execution time and the element temperature of the PM sensor 2. In FIG. 8, the horizontal axis represents time whereas the vertical axis represents the element temperature. Curve (a) in FIG. 8 indicates temperature changes encountered when the PM reset is performed on the PM sensor in which the PM is accumulated. Curve (b), on the other hand, indicates temperature changes encountered when the PM reset is performed on the PM sensor in which the PM is not accumulated.

As shown in FIG. 8, while the PM reset is being performed, the element temperature of the PM sensor in which the PM is accumulated and the element temperature of the PM sensor in which the PM is not accumulated both rise due to heating by the heater 16. In the PM sensor in which the PM is accumulated, however, the PM begins to burn. Thus, heat generated by the burning PM raises the element temperature to a greater extent than provided by the heat generated by the heater 16. Therefore, when the PM begins to burn after the execution of the PM reset, the element temperature of the PM sensor in which the PM is accumulated rises higher than the element temperature of the PM sensor in which no PM is burning. When, sooner or later, no more heat is generated by the burning PM as the PM is completely burned and eliminated, the element temperature of the PM sensor in which the PM is accumulated decreases and equals the element temperature of the PM sensor in which the PM is not accumulated.

The amount of burned PM correlates with the amount of generated heat. The larger the amount of burned PM, the larger the amount of generated heat. Therefore, the progress of PM burning can be determined by detecting the amount of heat generated by the currently burning PM. The second embodiment uses this relationship and terminates the PM reset when the amount of heat generated by the burning PM Q reaches a reference heat generation amount $\alpha$. This makes it possible to stop the burning of the PM at a stage before the PM is completely burned and eliminated and ensure that the amount of PM remaining on the element surface is equal to the reference PM amount.

The amount of generated heat Q is a value obtained by subtracting from the detected element temperature the element temperature reached when the PM sensor in which the PM is not accumulated is heated by the heater 16 in the same manner as for the execution of the PM reset. The amount of generated heat Q can be determined from the relationship between the present time, the amount of power supplied to the heater 16, and the element temperature. The relationship is predetermined by experiment or the like and stored as a map in the control device. During actual control, the map is used to determine the amount of generated heat Q in accordance, for instance, with the element temperature and the present time.

The reference heat generation amount $\alpha$ relative to the amount of generated heat Q is set to a value close to the upper-limit value of a heat generation amount range within which the PM remains on the element section surface to the extent that the amount of PM remaining in the PM sensor 2 forms an electrically conductive path between the electrodes 8 and 10 at one or more spots, that is, to the extent that the dead zone does not arise even immediately after the PM reset performed on the PM sensor 2. This value is predetermined by experiment or the like and stored in the control device. In the second embodiment, it is assumed that the PM reset starts when the amount of accumulated PM is estimated to be equal to a predetermined amount, and that the reference heat generation amount $\alpha$ relative to the amount of generated heat Q is a fixed value.

Figure 9:
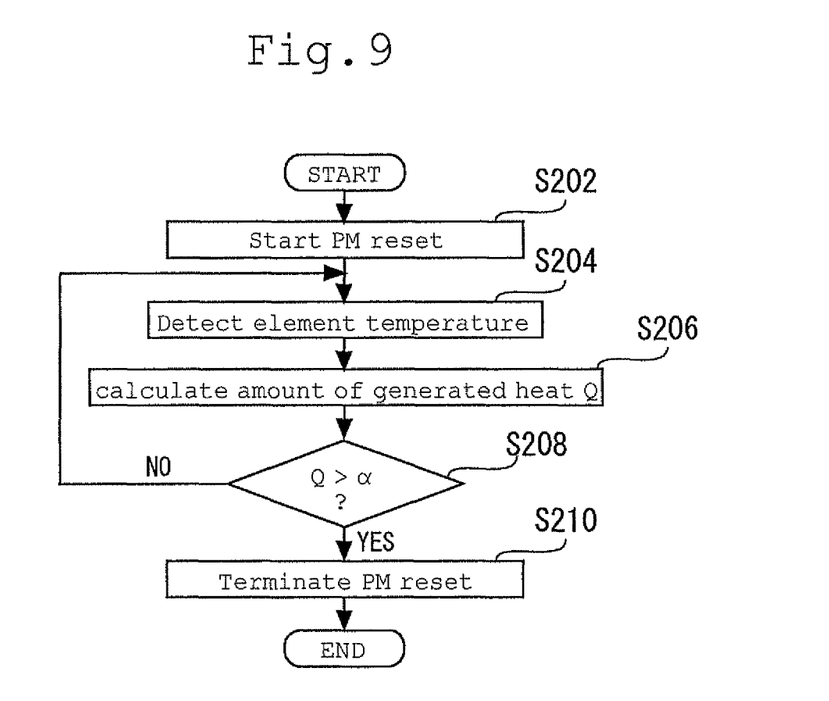
FIG. 9 is a flowchart illustrating a control routine that is executed by the control device in the second embodiment of the present invention.

FIG. 9 is a flowchart illustrating a control routine that is executed by the control device in the second embodiment of the present invention. The routine shown in FIG. 9 first performs step S202 in which the heater 16 is energized to start the PM reset. In the next step, which is step S204, the routine detects the element temperature. The element temperature is detected in the control device while the outputs of the temperature sensors 14 installed beneath the electrodes 8, 10 are used as input information.

Next, the routine proceeds to step S206 and calculates the amount of generated heat Q. The amount of generated heat Q is the amount of heat generated by burning the PM. The relationship between the amount of generated heat Q, time, the amount of power supplied to the heater 16, and the like is stored in the control device. The amount of generated heat Q is calculated in accordance with the stored relationship.

Next, the routine proceeds to step S208 and judges whether the amount of generated heat Q is larger than the reference heat generation amount $\alpha$. When the judgment result obtained in step S208 does not indicate that the amount of generated heat Q is larger than the reference heat generation amount $\alpha$, the routine returns to step S204, detects the element temperature, calculates the amount of generated heat Q, proceeds to step S208 for judgment purposes. The routine repeats steps S204 to S208 until the amount of generated heat Q is larger than the reference heat generation amount $\alpha$.

When, on the other hand, the judgment result obtained in step S208 indicates that the amount of generated heat Q is larger than the reference heat generation amount $\alpha$, the routine proceeds to step S210 and terminates the PM reset. More specifically, the routine shuts off the power supply to the heater 16. This ensures that the PM reset can be terminated while the amount of PM remaining in the PM sensor 2 is equal to the reference PM amount, which represents the required amount of PM. Subsequently, the current process terminates.

As described above, the second embodiment has been described on the assumption that whether the PM reset should be terminated is determined by judging whether the amount of generated heat Q is larger than the reference heat generation amount $\alpha$. The amount of generated heat Q depends on the burning of the PM. It increases with an increase in the amount of PM that is burned and eliminated. Therefore, when whether the PM reset should be terminated is determined in accordance with the amount of generated heat Q, the burning of the PM can be terminated at an appropriate stage at which the burning of the PM has progressed to a certain extent. This makes it possible to terminate the PM reset while an appropriate amount of PM remains. Consequently, immediately after the PM reset is terminated, changes in the output of the PM sensor 2, which are based on the amount of accumulated PM, can be detected to start measuring the amount of PM.

In the second embodiment, the element temperature is detected in accordance with the output of the temperature sensors 14 installed beneath the electrodes 8, 10. Hence, changes in the temperatures of the electrodes 8, 10 can be detected with high sensitivity and high accuracy. Therefore, the amount of heat generated Q due to the burning of the PM can be properly detected with high accuracy. This makes it possible to terminate the PM reset at an optimum stage. However, the present invention is not limited to the use of such element temperature detection means. For example, an element temperature sensor may alternatively be embedded into a certain portion of the insulation layer, positioned away from the electrodes 8, 10, and used to detect the element temperature. Another alternative is to detect the element temperature in accordance with changes in the impedance between the electrodes 8 and 10 and without installing the temperature sensors 14.

The second embodiment has been described on the assumption that whether the PM reset should be terminated is determined by calculating the amount of generated heat Q and judging whether the amount of generated heat Q is larger than the reference heat generation amount α. However, the present invention is not limited to the use of the above method. As described above, the amount of generated heat Q gradually increases during a period after the beginning of PM burning; however, the element temperature rise rate of the PM sensor 2 increases during this period. Therefore, when, for instance, the amount of change in the element temperature of the PM sensor 2 (sensor temperature differential value) exceeds its reference value, whether the PM reset should be terminated may be determined. The reference value may be set to be close to the upper-limit value of an element temperature change range within which the amount of remaining PM is equal to the reference PM amount despite the PM reset.

Further, the total amount of PM burned by the PM reset correlates with the integrated value of the amount of generated heat Q. Therefore, the integrated value of the amount of heat generated since the beginning of the PM reset may be calculated. When the integrated value of the amount of generated heat exceeds a reference amount, the reset of the PM sensor 2 may be terminated. The reference amount may be close to the total amount of heat generated when the PM is burned and decreased to the reference PM amount.

The second embodiment has been described on the assumption that a fixed value is used as the reference heat generation amount α for judgment relative to the amount of generated heat Q, the reference value for judgment on the basis of a temperature change amount, or the reference amount for judgment on the basis of the integrated value. However, the present invention is not limited to the use of such a fixed value. For example, the total amount of heat generated during the PM reset varies with the amount of PM that is actually burned and eliminated. It is therefore conceivable that the amount of generated heat Q, a temperature change value, and an integrated heat generation amount prevailing when the amount of PM remaining in the PM sensor 2 is equal to the reference PM amount vary with the amount of PM accumulated immediately before the start of the PM reset. Consequently, when, for instance, the start of the PM reset is to be determined only in accordance with the elapsed time after the last PM reset or it is anticipated that the amount of PM accumulated at the beginning of the PM reset may vary, more effective results will be obtained by accordingly set the reference heat generation amount α, a reference temperature change amount, and a reference amount for the integrated value, which serve as the reference for terminating the PM reset.

The second embodiment has been described on the assumption that whether the PM reset should be terminated is determined in accordance with the amount of generated heat (or the temperature change amount or the integrated heat generation amount). However, the present invention is not limited to the use of such a method. For example, as is the case with the first embodiment, the PM reset may be terminated when a predetermined reference time has elapsed and the reference heat generation amount is exceeded by the amount of generated heat. When coordinated control is exercised as described above to set the reference time for the PM reset, the amount of generated heat can be investigated at a stage where the PM reset has been performed for an appropriate period of time. Consequently, the amount of PM remaining on the element section surface equals the reference PM amount with increased certainty.

Further, if the sensor output is not decreased even after step S208 is repeated a number of times equal to the reference count to determine whether or not to terminate the PM reset, the routine may conclude that the PM sensor 2 is faulty, as is the case with the first embodiment.

In the second embodiment, the "temperature detection means" according to the present invention is implemented when the process in step S204 is performed; the "heat generation amount calculation means" is implemented when the process in step S206 is performed; the "particulate matter amount judgment means" is implemented when the process in step S208 is performed; and the "elimination process control means" is implemented when the process in step S210 is performed.

Third Embodiment

The system according to a third embodiment of the present invention has the same configuration as the system according to the first embodiment. In the third embodiment, only the sensor output is used to determine whether the PM reset should be terminated. More specifically, when the PM reset begins, the system according to the third embodiment supplies a pulse voltage to the heater 16. In other words, the power supply to the heater 16 is turned on and off at very short time intervals. Repeatedly turning on and off the power supply for a short period of time locally heats a region close to the electrodes 8, 10.

Whether the PM reset should be terminated is determined in accordance with the sensor output. As described earlier, the resistance value between the electrodes 8 and 10, which corresponds to the sensor output, correlates with the amount of accumulate PM. While the voltage remains unchanged, the sensor output decreases with a decrease in the amount of accumulated PM. Therefore, when the sensor output decreases below the reference output at a predetermined voltage, the system according to the third embodiment terminates the PM reset because it concludes that the amount of PM accumulated in the PM sensor 2 is decreased to the reference PM amount.

Even when the amount of accumulated PM remains unchanged, the sensor output varies with the element temperature. In other words, the sensor output for a fixed amount of accumulated PM increases with an increase in the element temperature and decreases with a decrease in the element temperature. Particularly, the system according to the third embodiment supplies electrical power to the heater 16 in a pulsed manner. This repeatedly causes the electrodes 8, 10 to be locally heated for a short period of time. Hence, while the PM reset is being performed, the element temperature of the PM sensor 2 greatly changes and does not always remain the same.

As such being the case, the system according to the third embodiment corrects the reference output, which is the sensor output for the reference PM amount, in accordance with the prevailing temperature. Correction values used for such a correction are predetermined, for instance, by conducting an experiment to determine how the reference output for the reference PM amount varies with the temperature. The relationship between temperatures, reference output, and correction values, which is determined as described above, is stored as a map in the control device. When actual control is exercised, the map is used to calculate the correction value to be used.

Figure 10:
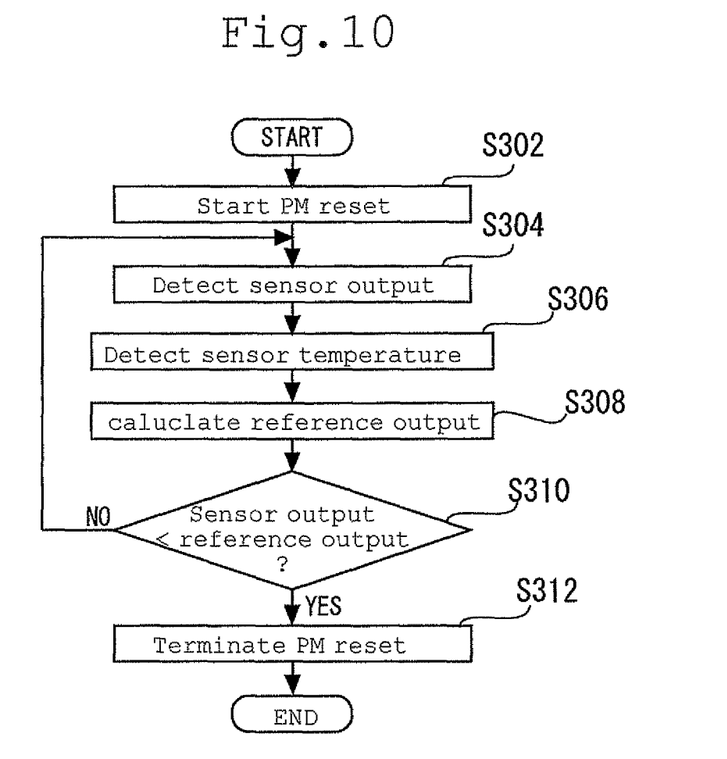
FIG. 10 is a flowchart illustrating a control routine that is executed by the control device in the third embodiment of the present invention.

FIG. 10 is a flowchart illustrating a control routine that is executed by the control device in the third embodiment of the present invention. The routine shown in FIG. 10 first performs step S302. In step S302, the PM reset begins so that electrical power is supplied to the heater 16 in a pulsed manner.

Next, the routine proceeds to step S304 and detects the sensor output. The sensor output is detected in the control device as the value of an electrical current between the electrodes 8 and 10 of the PM sensor 2. Next, the routine performs step S306 to detect a sensor temperature. The sensor temperature is detected in the control device while the outputs of the temperature sensors (thermocouples) 14 installed beneath the electrodes 8, 10 are used as input information.

Next, the routine performs step S308 to calculate the reference output. The reference output is calculated by correcting a stored output value in accordance with the temperature. A correction value used for such a correction is determined by acquiring a value according to the temperature from the map stored in the control device.

Next, the routine performs step S310 to judge whether the sensor output is lower than the reference output, which was set in step S308. When the judgment result obtained in step S310 does not indicate that the sensor output is lower than the reference output, the routine returns to step S304 and repeatedly detect the sensor output, detect the sensor temperature, calculate the reference output, and judge whether the sensor output is lower than the reference output (steps S304 to S310).

When the judgment result obtained in step S310 indicates that the sensor output is lower than the reference output, the routine proceeds to step S312 and terminates the PM reset. This brings the current process to an end.

As described above, the system according to the third embodiment heats the element section in a pulsed manner. Further, the heater 16 is patterned so as to particularly heat the comb-shaped portions of the electrodes 8, 10. Therefore, when the PM reset is performed, the comb-shaped portions of the electrodes 8, 10 can be locally heated for a short period of time. This makes it possible to prevent the whole element section from being excessively heated and reduce the power consumption during the PM reset.

Moreover, when the sensor output is lower than the reference output, the system according to the third embodiment terminates the PM reset. This makes it possible to ensure that the amount of PM remaining in the PM sensor 2 is equal to the reference PM amount, which represents the required amount of PM. Thus, the period during which the amount of PM can be measured by the PM sensor 2 can be lengthened by eliminating or shortening the dead zone prevailing immediately after the PM reset.

In addition, the reference output, which is used as the basis for determining whether or not to terminate the PM reset, is corrected in accordance with the temperature. Therefore, a proper reference output corresponding to the reference PM amount can be used to accurately determine whether the amount of PM is decreased.

The third embodiment has been described on the assumption that the reference output is corrected in accordance with the temperature. However, the present invention is not limited to the use of such a reference output. As is the case with the first embodiment, a fixed reference output may be stored for use. In such an instance, too, electrical power can be supplied in a pulsed manner to perform the PM reset while suppressing an excessive temperature rise in the vicinity of the electrodes 8, 10. This pulsed power supply to the heater 16 may also be applicable to the first and second embodiments.

The third embodiment has been described on the assumption that electrical power is supplied to the heater 16 in a pulsed manner. However, the present invention is not limited to a case where electrical power is supplied to the heater 16 in a pulsed manner. For example, the PM reset may be performed by supplying a DC current to the heater 16, as is the case with the first and second embodiments. Even when such an alternative power supply method is used, the PM reset can be terminated when the sensor output is lower than the reference output (corrected value). Consequently, it is possible to prevent the PM from being excessively eliminated.

The third embodiment has been described on the assumption that the reference output is corrected in accordance with the temperature. This correction is particularly effective in a situation where the temperature is likely to vary due, for instance, to pulsed heating. However, a scheme for correcting the reference output in accordance with the temperature, which has been described in connection with the third embodiment, is also applicable to the reference output according to the first embodiment.

Further, the reference time setting, which is performed for the PM reset according to the first embodiment, may be used in conjunction with the third embodiment so that whether the sensor output is lower than the corrected reference output is determined only when the PM reset is performed for the reference time.

In the third embodiment, the "sensor output detection means" according to the present invention is implemented when the process in step S304 is performed; the "temperature detection means" is implemented when the process in step S306 is performed; the "reference output setup means" is implemented when the process in step S308 is performed; the "particulate matter amount judgment means" is implemented when the process in step S310 is performed; and the "elimination process control means" is implemented when the process in step S312 is performed.

When a numerical value is used to indicate, for instance, the number of elements or the quantity, volume, or range of the elements for the purpose of describing the foregoing embodiments, the present invention is not limited to such a numerical value except when the numerical value is used to expressly describe the elements or clearly state the principles of the elements. Further, structures and arrangements describing the foregoing embodiments are not always essential to the present invention except when such structures and arrangements are used to expressly describe the elements or clearly state the principles of the elements.

DESCRIPTION OF NOTATIONS

2 Sensor
6 element section
8, 10 electrode
12 insulation layer
14 temperature sensors
16 heater

The invention claimed is:
1. A control device for an internal combustion engine, comprising:
    a particulate matter sensor, for measuring an amount of particulate matter in a gaseous body, that includes a pair of electrodes disposed at a distance from each other;
    elimination means for burning and eliminating particulate matter attached to the particulate matter sensor;

particulate matter amount judgment means for judging whether the amount of particulate matter attached to the particulate matter sensor is smaller than a reference particulate matter amount that is predefined as a minimum amount of remaining particulate matter required to bring the pair of electrodes into electrical conduction at one or more spots; and elimination process control means for causing the elimination means to terminate a process of eliminating the particulate matter when the amount of particulate matter is judged to be smaller than the reference particulate matter amount.

2. The control device according to claim 1, further comprising:

reference time setup means for setting, as a reference time, a time required for the elimination process to decrease the amount of particulate matter to the reference particulate matter amount in accordance with an operating status of the internal combustion engine;

wherein the particulate matter amount judgment means judges whether the amount of particulate matter is smaller than the reference particulate matter amount by determining whether the elimination process is performed for the reference time.

3. The control device according to claim 1 further comprising:

sensor output detection means for detecting an output of the particulate matter sensor;

wherein the particulate matter amount judgment means judges whether the amount of particulate matter is smaller than the reference particulate matter amount by determining whether the output of the particulate matter sensor is lower than a reference output that is set as a particulate matter sensor output that is equivalent to the reference particulate matter amount.

4. The control device according to claim 3, further comprising:

temperature detection means for detecting a temperature of an element section of the particulate matter sensor; and reference output setup means for setting the reference output in accordance with the temperature detected by the temperature detection means.

5. The control device according to claim 1 further comprising:

temperature detection means for detecting a temperature of the particulate matter sensor; and heat generation amount calculation means for calculating an amount of heat generated by the particulate matter sensor in accordance with the temperature detected by the temperature detection means;

wherein the particulate matter amount judgment means judges whether the amount of particulate matter is smaller than the reference particulate matter amount by determining whether the amount of generated heat is larger than a reference heat generation amount.

6. The control device according to claim 1, further comprising:

temperature detection means for detecting a temperature of the particulate matter sensor;

heat generation amount calculation means for calculating an amount of heat generated by the particulate matter sensor in accordance with the temperature detected by the temperature detection means; and integrated heat generation amount detection means for detecting an integrated amount of heat generated since a beginning of the elimination process;

wherein the particulate matter amount judgment means judges whether the amount of particulate matter is smaller than the reference particulate matter amount by determining whether the integrated amount is larger than a reference integrated heat generation amount.

7. The control device according to claim 1 further comprising:

temperature detection means for detecting a temperature of the particulate matter sensor; and temperature change calculation means for calculating a change in the temperature of the particulate matter sensor;

wherein the particulate matter amount judgment means judges whether the amount of particulate matter is smaller than the reference particulate matter amount by determining whether the temperature change is smaller than a reference temperature change amount.

8. The control device according to claim 4, wherein the temperature detection means is a temperature sensor that is installed near the pair of electrodes of the particulate matter sensor.

9. The control device according to claim 1, wherein the elimination means is a heater installed near the pair of electrodes; and wherein the elimination process control means supplies electrical power having a fixed pulse width to the heater to heat the pair of electrodes and burn the particulate matter.

10. The control device according to claim 1, wherein the elimination means is a heater installed near the pair of electrodes; wherein the pair of electrodes each have a dense area where the electrodes are relatively densely disposed; and wherein the heater mainly heats the dense area of the pair of electrodes.

11. The control device according to claim 2, further comprising:

sensor output detection means for detecting an output of the particulate matter sensor;

wherein the particulate matter amount judgment means judges whether the amount of particulate matter is smaller than the reference particulate matter amount by determining whether the output of the particulate matter sensor is lower than a reference output that is set as a particulate matter sensor output that is equivalent to the reference particulate matter amount.

12. The control device according to claim 11, further comprising:

temperature detection means for detecting a temperature of an element section of the particulate matter sensor; and reference output setup means for setting the reference output in accordance with the temperature detected by the temperature detection means.

13. The control device according to claim 2, further comprising:

temperature detection means for detecting a temperature of the particulate matter sensor; and heat generation amount calculation means for calculating an amount of heat generated by the particulate matter sensor in accordance with the temperature detected by the temperature detection means;

wherein the particulate matter amount judgment means judges whether the amount of particulate matter is smaller than the reference particulate matter amount by determining whether the amount of generated heat is larger than a reference heat generation amount.

14. The control device according to claim 2, further comprising:
- temperature detection means for detecting a temperature of the particulate matter sensor;
- heat generation amount calculation means for calculating an amount of heat generated by the particulate matter sensor in accordance with the temperature detected by the temperature detection means; and
- integrated heat generation amount detection means for detecting an integrated amount of heat generated since a beginning of the elimination process;
- wherein the particulate matter amount judgment means judges whether the amount of particulate matter is smaller than the reference particulate matter amount by determining whether the integrated amount is larger than a reference integrated heat generation amount.

15. The control device according to claim 2, further comprising:
- temperature detection means for detecting a temperature of the particulate matter sensor; and
- temperature change calculation means for calculating a change in the temperature of the particulate matter sensor;
- wherein the particulate matter amount judgment means judges whether the amount of particulate matter is smaller than the reference particulate matter amount by determining whether the temperature change is smaller than a reference temperature change amount.

16. The control device according to claim 12, wherein the temperature detection means is a temperature sensor that is installed near the pair of electrodes of the particulate matter sensor.

17. The control device according to claim 2, wherein the elimination means is a heater installed near the pair of electrodes; and wherein the elimination process control means supplies electrical power having a fixed pulse width to the heater to heat the pair of electrodes and burn the particulate matter.

18. The control device according to claim 2, wherein the elimination means is a heater installed near the pair of electrodes; wherein the pair of electrodes each have a dense area where the electrodes are relatively densely disposed; and wherein the heater mainly heats the dense area of the pair of electrodes.

19. The control device according to claim 1, wherein the reference particulate matter amount is determined based on an amount of remaining particulate matter required to bring, in accordance with changes in amount of attached particulate matter, a change of the output of the particulate matter sensor.

20. The control device according to claim 2, wherein the reference particulate matter amount is determined based on an amount of remaining particulate matter required to bring, in accordance with changes in amount of attached particulate matter, a change of the output of the particulate matter sensor.

21. A control device for an internal combustion engine, comprising:
- a particulate matter sensor, that includes a pair of electrodes disposed at a distance from each other, for measuring an amount of particulate matter in a gaseous body in accordance with the resistance between the pair of the electrodes;
- elimination means for burning and eliminating particulate matter attached to the particulate matter sensor;
- elimination process control means for terminating a process of eliminating the particulate matter when the amount of the particulate matter attached to the particulate matter sensor decrease to the amount of remaining particulate matter required, immediately after the process of eliminating is terminated, to bring a change of the output of the particulate matter sensor in accordance with changes in amount of attached particulate matter.

* * * * *